(12) United States Patent
Abfall et al.

(10) Patent No.: US 9,908,688 B2
(45) Date of Patent: Mar. 6, 2018

(54) VENTED DISPENSING DEVICE

(71) Applicants: Tony J. Abfall, Mount Prospect, IL (US); Kara Lineal, Northbrook, IL (US); Paul Holbrook, Buffalo Grove, IL (US)

(72) Inventors: Tony J. Abfall, Mount Prospect, IL (US); Kara Lineal, Northbrook, IL (US); Paul Holbrook, Buffalo Grove, IL (US)

(73) Assignee: Digital Innovations LLC, Arlington Heights, IL (US)

( * ) Notice: Subject to any disclaimer, the term of this patent is extended or adjusted under 35 U.S.C. 154(b) by 0 days.

(21) Appl. No.: 15/341,880

(22) Filed: Nov. 2, 2016

(65) Prior Publication Data
US 2017/0203891 A1     Jul. 20, 2017

Related U.S. Application Data

(63) Continuation of application No. 14/735,003, filed on Jun. 9, 2015, now abandoned, which is a continuation of application No. 13/954,041, filed on Jul. 30, 2013, now abandoned, which is a continuation of application No. 13/288,742, filed on Nov. 3, 2011, now abandoned, which is a continuation-in-part of application No. 12/712,569, filed on Feb. 25, 2010, now Pat. No. 8,523,020.

(60) Provisional application No. 61/155,432, filed on Feb. 25, 2009.

(51) Int. Cl.
*B65D 83/28* (2006.01)
*A61L 9/12* (2006.01)
*A61L 9/14* (2006.01)
*B65D 51/28* (2006.01)
*B65D 83/38* (2006.01)
*B65D 51/16* (2006.01)

(52) U.S. Cl.
CPC .............. *B65D 83/285* (2013.01); *A61L 9/12* (2013.01); *A61L 9/14* (2013.01); *B65D 51/16* (2013.01); *B65D 51/28* (2013.01); *B65D 83/38* (2013.01)

(58) Field of Classification Search
CPC ............ A61L 9/12; A61L 9/14; B65D 83/285
See application file for complete search history.

(56) References Cited

U.S. PATENT DOCUMENTS

| | | |
|---|---|---|
| 1,202,642 A | 10/1916 | Allen |
| 1,255,772 A | 2/1918 | Miller |
| 1,280,541 A | 10/1918 | Potthoff |
| 1,355,482 A | 10/1920 | Lees |
| 1,523,297 A | 1/1925 | Savery |
| 1,582,645 A | 4/1926 | Findley |
| 1,615,319 A | 1/1927 | Wynn |
| 1,657,050 A | 1/1928 | Walter |
| 1,879,517 A | 9/1932 | Robotham |

(Continued)

FOREIGN PATENT DOCUMENTS

EP     1 935 512 A1     6/2008

*Primary Examiner* — Ryan Reis
(74) *Attorney, Agent, or Firm* — Clifford H. Kraft

(57) ABSTRACT

The dispensing device provides dispensable material in a closable container in concert with a corresponding accessory so that the container and the accessory can be commonly stored when not in use, and further provides a ventilated storage volume within the device that can facilitate drying and aerating the accessory.

8 Claims, 14 Drawing Sheets

(56) References Cited

U.S. PATENT DOCUMENTS

| | | | |
|---|---|---|---|
| 1,942,953 A | 1/1934 | Bennett | |
| 2,292,413 A | 8/1942 | Taylor | |
| 2,401,318 A | 6/1946 | Robinson et al. | |
| 2,438,129 A | 3/1948 | Rich | |
| 2,620,085 A | 12/1952 | Baldanza | |
| 2,657,090 A | 10/1953 | Meek | |
| 2,765,194 A | 10/1956 | Will | |
| 2,769,565 A | 11/1956 | Sottile | |
| 2,783,084 A | 2/1957 | Paxton | |
| 2,864,118 A | 12/1958 | Adams et al. | |
| 2,935,186 A | 5/1960 | Clark | |
| 3,330,481 A * | 7/1967 | Dearling | B05B 11/04 222/402.13 |
| 3,508,559 A | 4/1970 | Wolfe | |
| 3,662,913 A | 5/1972 | Mascia | |
| 3,746,158 A | 7/1973 | Connick | |
| 3,763,998 A | 10/1973 | Fisher | |
| 3,768,688 A | 10/1973 | Linke | |
| 3,848,803 A | 11/1974 | Levey | |
| 3,940,024 A * | 2/1976 | Russo | B65D 83/205 222/182 |
| 3,972,473 A * | 8/1976 | Harrison | B65D 83/285 239/326 |
| 4,084,732 A * | 4/1978 | Dearling | A61L 9/14 222/402.17 |
| 4,200,229 A * | 4/1980 | Spector | A61L 9/12 224/483 |
| 4,341,348 A * | 7/1982 | Dearling | A61L 9/12 239/326 |
| 4,436,224 A | 3/1984 | McInerny | |
| 4,516,676 A | 5/1985 | Cournoyer | |
| 4,522,298 A | 6/1985 | Weinberger | |
| 4,726,519 A * | 2/1988 | Muoio | A61L 9/14 222/331 |
| 4,759,501 A * | 7/1988 | Silvenis | A61L 9/14 239/289 |
| 4,818,134 A | 4/1989 | Tsai | |
| 4,927,284 A | 5/1990 | Tsai | |
| 4,953,999 A | 9/1990 | Rivers | |
| 4,974,727 A | 12/1990 | Karasin et al. | |
| 5,100,010 A | 3/1992 | Waters | |
| 5,769,263 A | 6/1998 | Willingham et al. | |
| 6,000,580 A | 12/1999 | Nilson | |
| 6,029,901 A | 2/2000 | Toy, II | |
| 6,170,651 B1 | 1/2001 | Taormina | |
| 6,321,937 B1 | 11/2001 | DeSimone et al. | |
| 6,536,977 B1 | 3/2003 | Hammel | |
| 6,883,989 B2 | 4/2005 | Kushner et al. | |
| 7,074,443 B2 | 7/2006 | Thomas et al. | |
| 7,225,950 B2 | 6/2007 | McKay | |
| 7,370,754 B2 | 5/2008 | Kushner | |
| 7,465,116 B2 | 12/2008 | Sorrell | |
| 7,585,125 B2 | 9/2009 | Muhlhausen et al. | |
| 7,681,809 B2 * | 3/2010 | Maget | A61L 9/12 222/187 |
| 7,743,947 B2 | 6/2010 | Flasch | |
| D630,010 S | 1/2011 | Brown | |
| 2007/0067934 A1 | 3/2007 | Osborne | |
| 2009/0032553 A1 | 2/2009 | Eddy | |
| 2011/0000977 A1 | 1/2011 | Withers | |

* cited by examiner

VENTED DISPENSING DEVICE

Parent application Ser. Nos. 13/954,041 and 14/016,184 are hereby incorporated by reference in their entireties. Application Ser. No. 14/735,003 is hereby incorporated by reference in its entirety.

The vented dispensing device can provide dispensable material in a closable container in concert with a suitable applicator so that the container and the applicator can be cooperatively stored when not in use. The dispensing device can further provide a ventilated storage volume within the device that can facilitate drying the applicator, for example when the dispensed container contents comprise liquids, and for aerating the applicator, for example to minimize mold growth and other unwanted conditions that can be minimized by air flow. Other benefits can be realized by the ventilated storage volume configuration beyond the aforementioned, including but not limited to dispersing fragrance and masking environmental odor.

SUMMARY OF THE INVENTION

In one embodiment, the vented dispensing device can comprise a dispensing accessory and a container. The container can comprise a dispensing nozzle for dispensing container contents, and a vented cover for retaining the dispensing accessory proximal to the container. The vented cover in use can connect to the container and can define an accessory storage volume between the vented cover and the container. The vented cover can have a vent opening extending through the vented cover to ventilate the storage volume; and at least part of the dispensing accessory can be confined within the storage volume when the vented cover is in use.

In another embodiment, the vented dispensing device can comprise a dispensing accessory and a container. The container can comprise a dispensing nozzle for dispensing container contents. The dispensing nozzle can have a trigger and a trigger cap, where the trigger cap can be connected to the container and spaced apart from the trigger. The trigger cap in use can limit contact between the dispensing accessory and the trigger. The container can further comprise a vented cover for retaining the dispensing accessory proximal to the container. The vented cover in use can connect to the container and can define an accessory storage volume between the vented cover and the container. The vented cover can have at least one vent opening extending through the vented cover to ventilate the storage volume, and at least part of the dispensing accessory can be confined within the storage volume when the vented cover is in use.

In another embodiment, the vented dispensing device can comprise a dispensing accessory and a container. The container can comprise a nozzle end, a reservoir end, and a trunk connecting the nozzle end and the reservoir end. The container can further comprise a dispensing nozzle connected to the nozzle end, the nozzle for dispensing container contents. The nozzle can comprise a trigger, with the trigger being movable to release container contents through the nozzle. The container can further comprise a trigger guard extending along a trigger perimeter, the trigger guard limiting access to the trigger across the perimeter. The container can further comprise a vented cover in use retaining the dispensing accessory proximal to the container. The vented cover can comprise an open end and vent end. The open end can be configured to receive the trunk, the nozzle end, and the nozzle, and to connect to the container proximal to the reservoir end. The vent end can comprise a plurality of vent openings through the vented cover, the vent openings positioned to facilitate airflow around the nozzle when the vented cover is in use. The vented cover in use can connect to the container to define an accessory storage volume between the vented cover and the container, and at least part of the dispensing accessory can be confined in the storage volume when the vented cover is in use.

FIGURES

DETAILED DESCRIPTION

Figure 1:
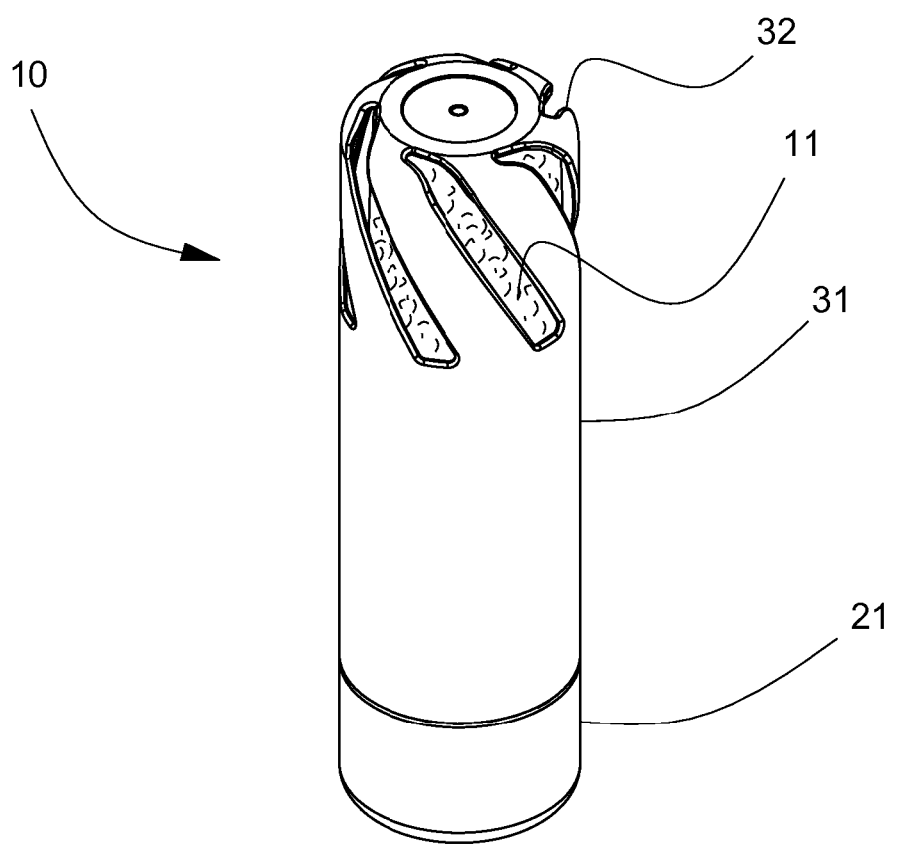
FIG. 1 is an isometric view of an embodiment of the dispensing device.

The vented dispensing device can comprise a dispensing accessory and a container. The container can hold dispensable material such as cleaning fluid, finishes like polish and wax, powder, compressed air and other gases, and various other materials and combinations thereof.

The container can comprise various geometric and organic shapes. The container can be cylindrical, prismatic, cone-shaped, and various shapes and combinations thereof.

The container can be configured with engagement features, for example, depressions, protrusions, hooks, forks, and various other features and combinations thereof.

The container can further comprise a plurality of content sections, for example, separate sections for holding different contents.

The container can comprise a nozzle end, a reservoir end, and a trunk connecting the nozzle end and the reservoir end. The container can be open at the nozzle end, and can have various other openings.

The dispensing accessory can be utilized to apply container contents, can be utilized to remove dispensed container contents, for example excess material, overspray, and used cleaning fluid, can be used to buff, polish, shine, and otherwise affect finish.

The dispensing accessory can be a towel, a soft pad, a sponge, and various other accessories and combinations thereof. The dispensing accessory can be a brush, a cotton ball, and a swab.

The container can comprise a dispensing nozzle for dispensing container contents. The dispensing nozzle can selectively open and close the container. The dispensing nozzle can close the container at the nozzle end.

The dispensing nozzle can comprise a pump, a valve, a hinged flap, and various dispensing mechanisms and combinations thereof. The dispensing nozzle can comprise an opening such as an orifice, an aperture, and an elongate tube. The dispensing nozzle can comprise a plurality of openings. The dispensing nozzle can have an open position and a closed position. The dispensing nozzle can have a plurality of open positions, for example, when utilized with a container having a plurality of content sections, the open positions from the plurality of open positions can correlate to respective container content sections.

The container can further comprise a vented cover. The vented cover can facilitate retaining the dispensing accessory proximal to the container. The vented cover in use can connect to the container and define an accessory storage volume between the vented cover and the container.

The vented cover can receive at least part of the container within the vented cover. For example, the vented cover can be configured to enclose the container including the nozzle within the storage volume. Alternatively, the vented cover can enclose the vented cover except for the nozzle within the storage volume. Alternatively, the vented cover can be configured to enclose the nozzle in one position, and to enclose the container except for the nozzle in another position. Alternatively, the vented cover can connect to the container and not receive a part of the container within the vented cover.

The vented cover can comprise a vent opening extending through the vented cover. The vent opening can facilitate air flow into and out of the accessory storage volume to ventilate the accessory storage volume.

The vent opening can be positioned on the vented cover to ventilate a predetermined part of the storage volume, for example, to ventilate the storage volume proximal to the nozzle. Similarly, other parts of the storage volume where moisture is likely to collect can be targeted by positioning the vent opening to ventilate the predetermined part of the storage volume. The vented cover can comprise an open end and a nozzle end and can be configured to receive the container including the nozzle through the open end so that the nozzle is positioned proximal the nozzle end when the vented cover is in use.

The vented cover, in use connected to the container, can confine at least part of the dispensing accessory within the accessory storage volume. Confining part of the dispensing accessory within the accessory storage volume can facilitate retaining the dispensing accessory proximal to the container when the dispensing accessory is not in use.

When the vented cover is in use and part of the dispensing accessory is confined within the accessory storage volume, the vent opening can facilitate drying the accessory and can prevent accumulation of excess container content on the accessory and within the storage volume.

The vented cover can comprise a plurality of vent openings. The plurality of vent openings can be positioned on the vented cover so that each vent opening ventilates one or more predetermined parts of the storage volume.

The vented cover can be configured to define a plurality of accessory storage volumes between the vented cover and the container, when the vented cover is in use. The vented cover can confine at least parts of dispensing accessories from a plurality of dispensing accessories within the plurality of accessory storage volumes.

The container can comprise a plurality of vented covers and each cover from the plurality of vented covers can connect to the container directly and can connect to the container via connecting to another cover from the plurality of vented covers.

Figure 2:
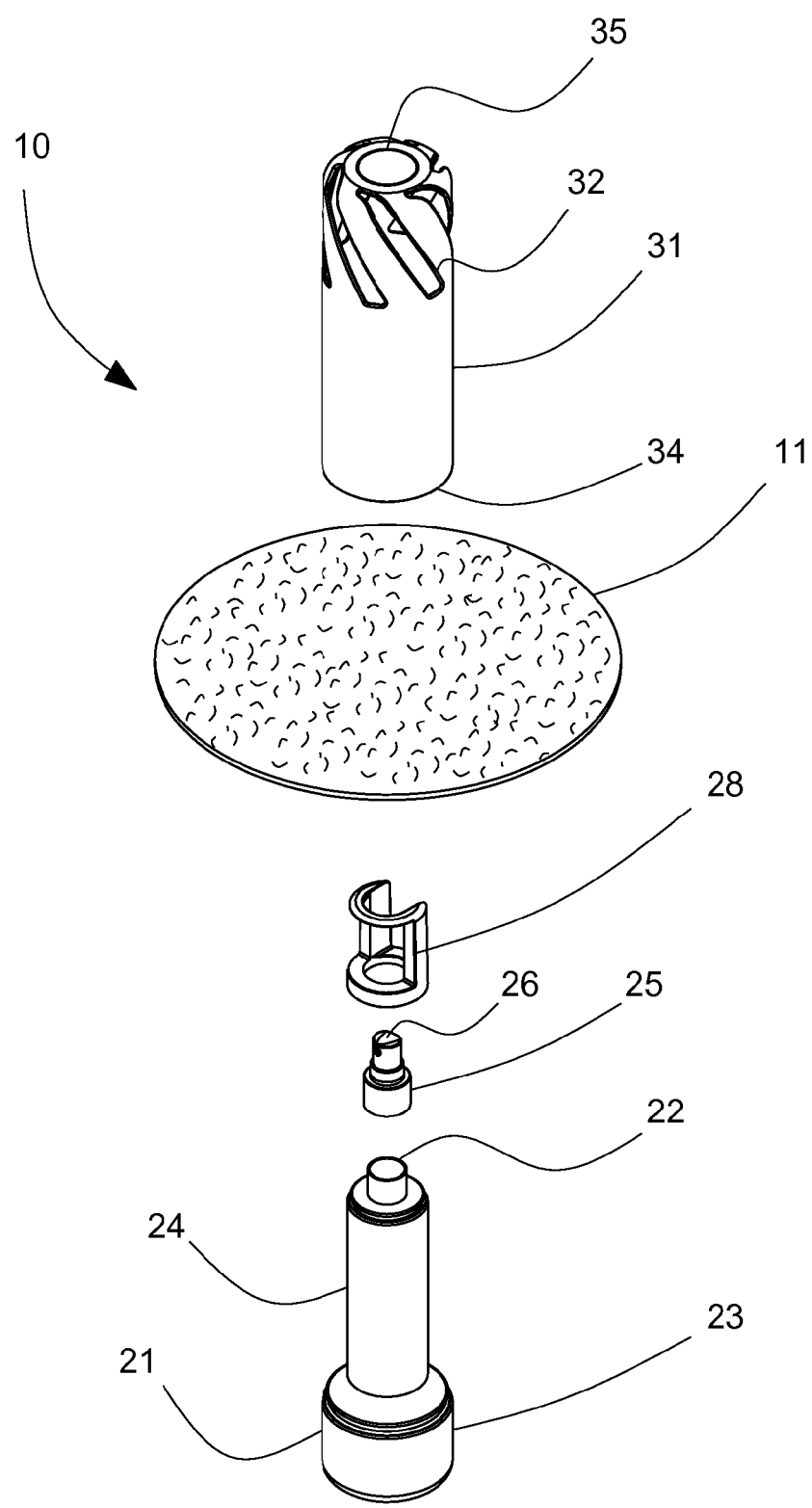
FIG. 2 is an exploded view of the above embodiment.
Figure 3:
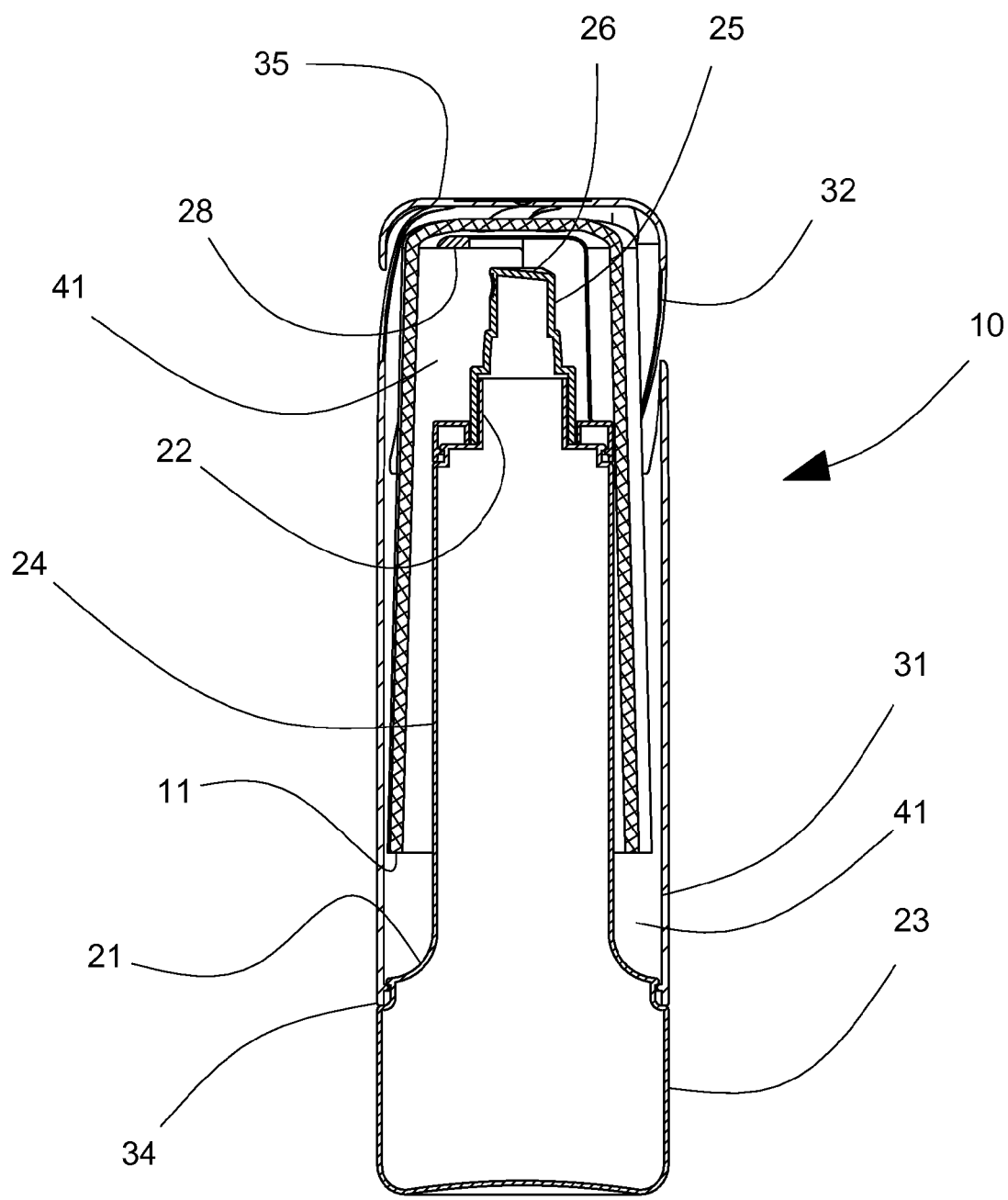
FIG. 3 is a side section view of the above embodiment.

In the embodiment of FIGS. 1, 2, and 3, the dispensing device 10 comprises a dispensing accessory 11, a container 21, a dispensing nozzle 25, and a vented cover 31.

The dispensing accessory 11 comprises a cloth-like accessory for applying, distributing, and removing dispensed container contents.

The container 21 comprises a generally cylindrically-shaped trunk 24 with a reduced neck at the nozzle end 22 and a larger cylindrically-shaped reservoir end 23. The nozzle 25 closes the container 21 at the nozzle end 22.

The vented cover 31 connects to the container 21 and defines an accessory storage volume 41 between the vented cover 31 and the container 21. In use, the vented cover 31 receives the container 21 through the vented cover open end 34 and connects to the container 21 proximal the container reservoir end 23. The vented cover 31 encloses the nozzle 25 within the accessory storage volume 41.

The vented cover 31 comprises a plurality of vent openings, such as the vent opening 32. The vent opening 32 extends through the vented cover 31 and enables air to flow through the vented cover 31 and facilitates ventilating the storage volume 41. In use connected to the container 21, the vent opening 32 is positioned at the vent end 35 to ventilate the storage volume 41 proximal to the nozzle 25.

As shown explicitly in FIGS. 1 and 3, the dispensing accessory 11 is confined within the storage volume 41 when the vented cover 21 is in use. The cloth-like accessory 11 can drape over the nozzle 25 and extend along the container trunk 24. With the vented cover 31 in use connected to the container 21, the dispensing accessory 11 is substantially confined within the accessory storage volume 41 between the vented cover 31 and the container 21.

Additionally, when the dispensing accessory 11 is confined within the storage volume 41 as shown in FIGS. 1 and 3, the vent opening 32 is positioned to ventilate the middle part of the dispensing accessory 11. Observations of common usage have shown that the middle part of the cloth-like accessory 11 can accumulate excess container contents and so benefits from maximum ventilation.

The nozzle can comprise a trigger for causing the nozzle to dispense container contents. The trigger can be movable to release container contents through the nozzle. The trigger can activate another component to cause release of container contents. The trigger can cause dispensing via various means and methods.

The trigger can comprise a spray head with a finger-positioning depression, a lever for pumping container contents from the container through the nozzle, a valve release actuator, and a pushbutton. The trigger can comprise various other mechanisms and indicators and combinations thereof, which facilitate dispensing container contents via the nozzle.

The nozzle 25 of the container 21 comprises a trigger 26. The trigger 26 is movable to release container contents, for example, to release pressurized gases.

The container can further comprise a trigger cap. The trigger cap can prevent unintentional trigger movement and can prevent accidental dispensing of the container contents. The trigger cap can be positioned proximal to the trigger and can limit contact between the dispensing accessory and the trigger, especially when the dispensing accessory is confined within the storage volume.

The trigger cap can enclose the trigger and can enclose the nozzle. Alternatively, the trigger cap can extend adjacent to the trigger to limit contact between the dispensing accessory and the trigger.

The trigger cap can comprise a trigger guard extending along a trigger perimeter, where the trigger perimeter at least party encircles the trigger. The trigger guard can limit access to the trigger across the perimeter and enable access to the trigger from other directions. The trigger guard can provide similar protection as the trigger cap against accidental discharge while still enabling selective access to the trigger while the trigger guard is in use.

Figure 4:
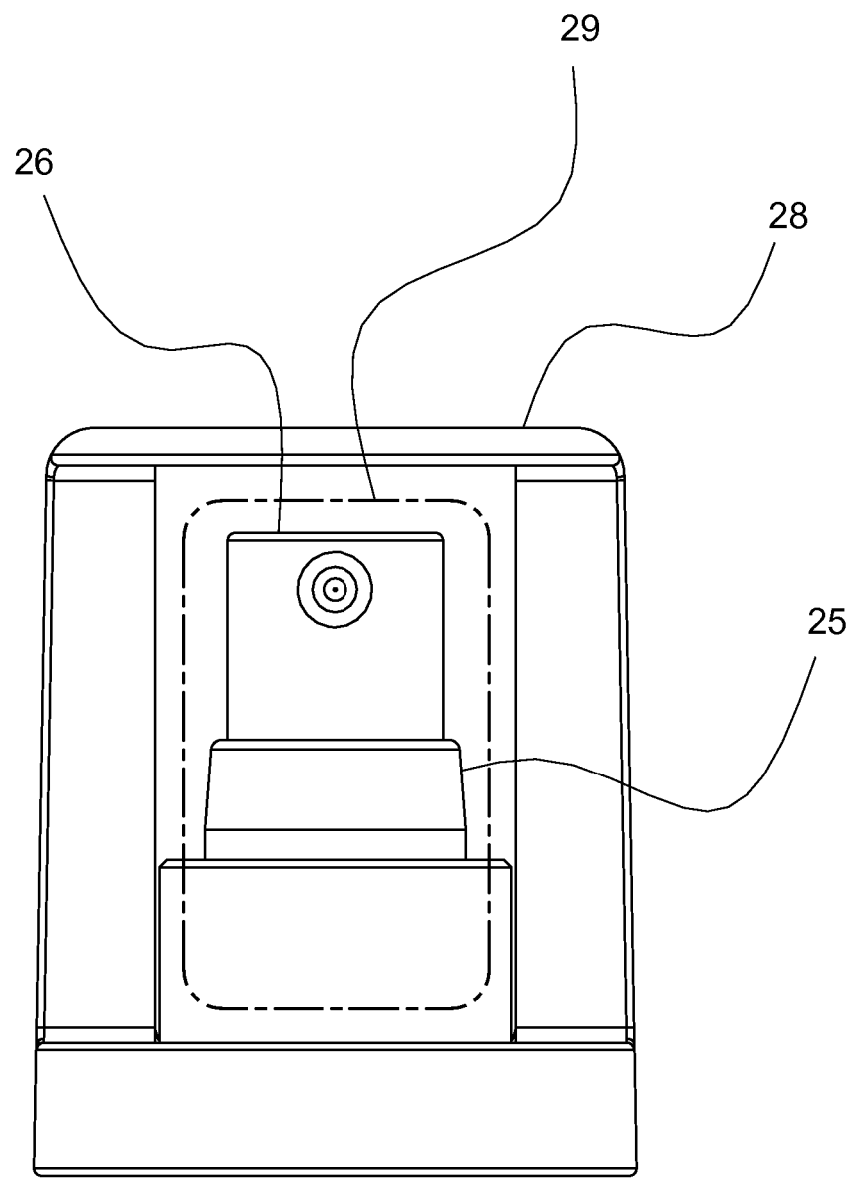
FIG. 4 is a front view of an embodiment of a dispensing nozzle with a trigger guard showing a trigger perimeter.

As shown in FIGS. 2, 3, and 4, the container 21 includes a trigger cap comprising a trigger guard 28. The trigger guard 28 extends over the trigger 26 along a trigger perimeter 29, and limits access to the trigger 26 across the trigger perimeter 29. With the trigger guard 28 in use, access to the trigger 26 is enabled through (but not across) the trigger perimeter 29. When the dispensing accessory 11 is confined within the storage volume 41, the dispensing accessory 11 can be spaced apart from the trigger 26 by the trigger guard 28 to prevent accidental discharge of container contents.

Figure 5:
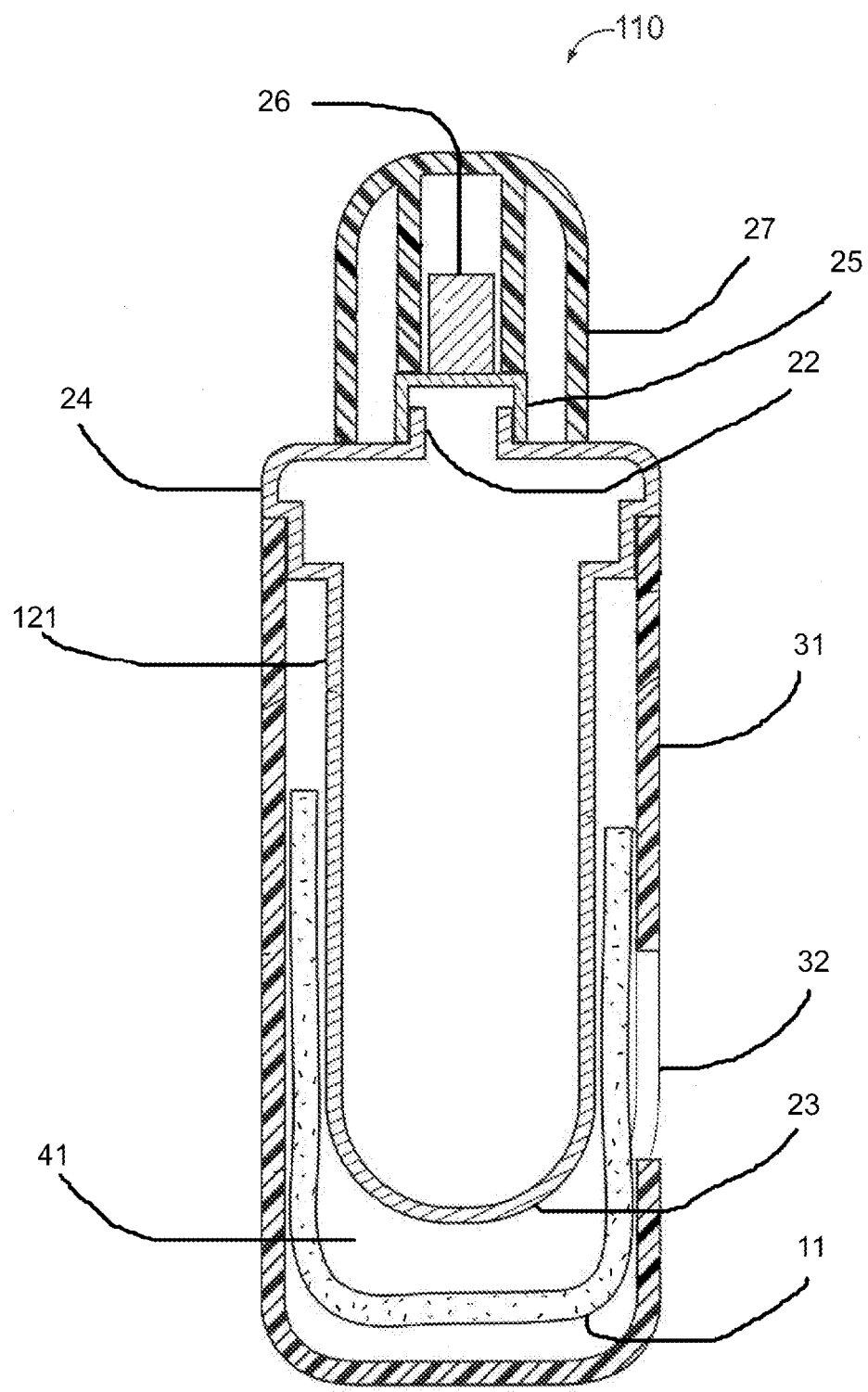
FIG. 5 is a side section view of another embodiment

In the embodiment shown in FIG. 5, the dispensing device 110 comprises a container 121. The container 121 is generally cylindrically-shaped including a reduced neck at the nozzle end 22 and a larger trunk 24 connecting the nozzle end 22 and the reservoir end 23.

The container 121 comprises a nozzle 25 with a trigger 26, where the nozzle 25 closes the container 121 at the nozzle end 22. The container 121 further comprises a trigger cap 27. The trigger cap 27 in use fully covers the trigger 26 to prevent accidental discharge.

The vented cover 31 of the dispensing device 110 connects to the container 121 proximal the trunk 24, enclosing the reservoir end 23 and not enclosing the nozzle 22 and the trigger cap 27. The dispensing accessory 11 is confined within the accessory storage volume 41 when the vented cover 31 is in use. The vented cover 31 comprises a plurality of vent openings, such as the vent opening 32, and the vent opening 32 is positioned on the vent cover 31 so that the storage volume 41 is ventilated proximal the dispensing accessory 11.

Figure 6:
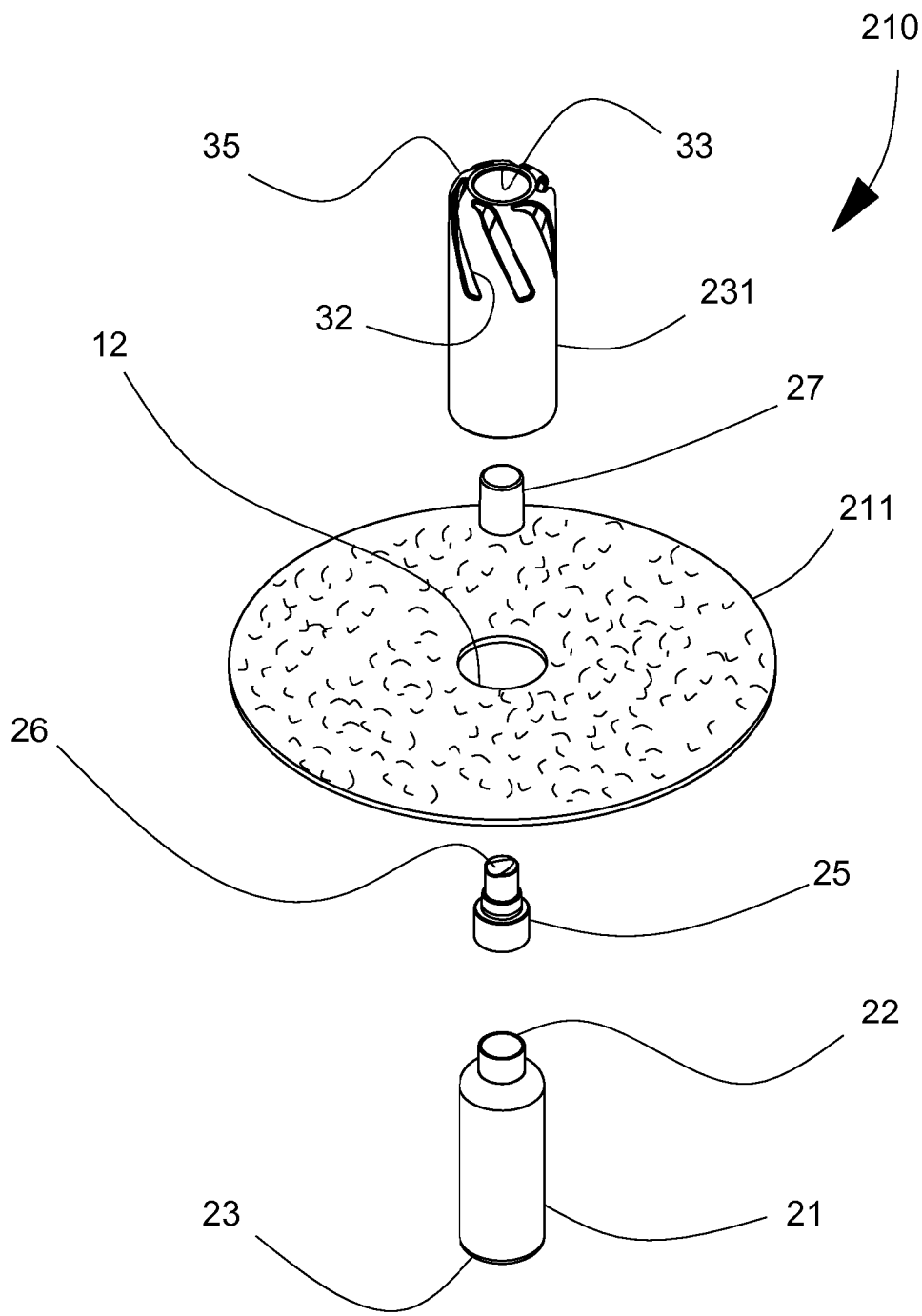
FIG. 6 is an exploded view of another embodiment including a trigger cap, a cover nozzle opening and an accessory nozzle opening.
Figure 7:
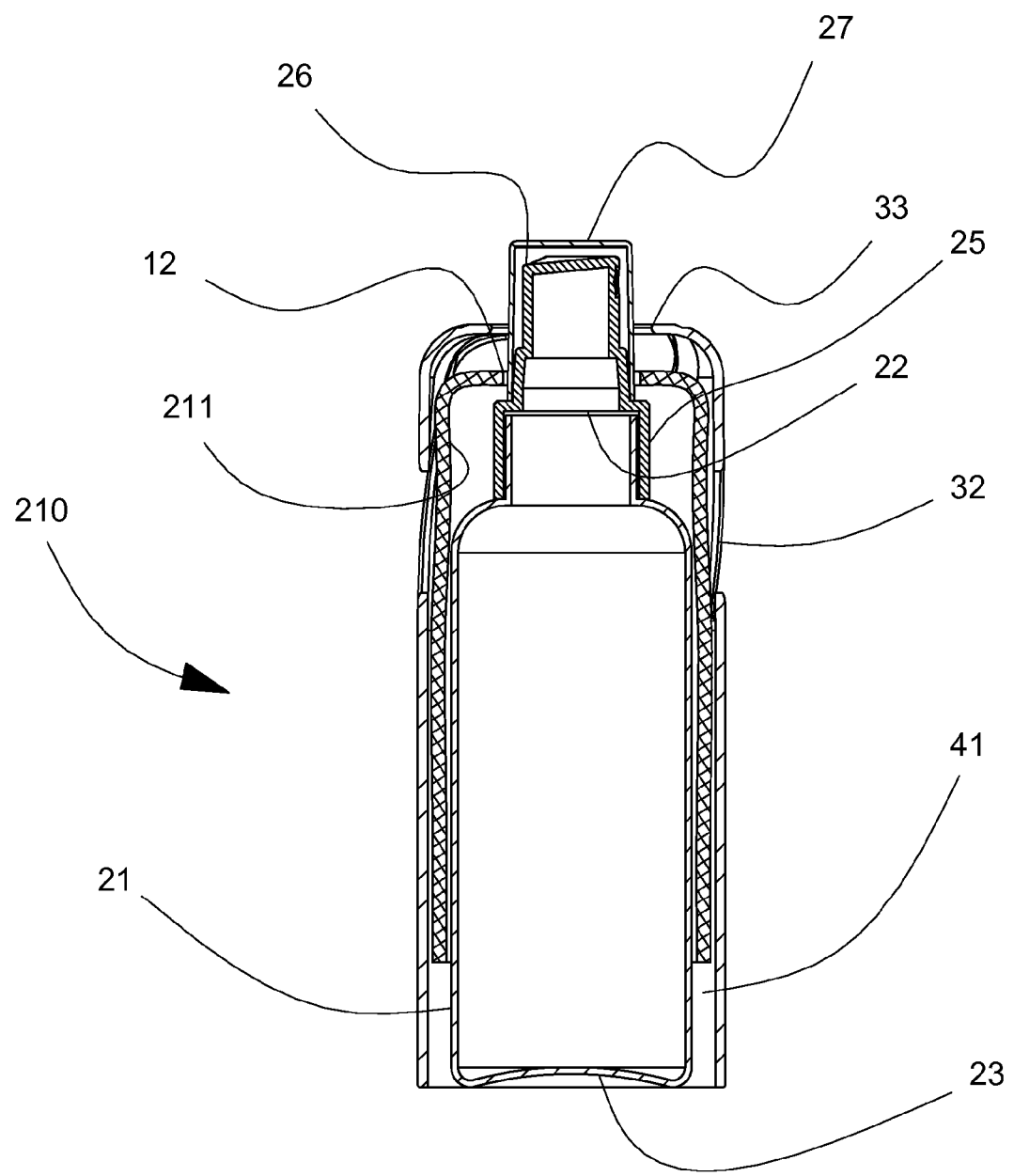
FIG. 7 is a side section view of the above embodiment.

In the embodiment shown in FIGS. 6 and 7, the dispensing device 210 comprises a container 21, a dispensing accessory 211, and a vented cover 231. The dispensing accessory 211 further comprises an accessory nozzle opening 12 through the middle part of the dispensing accessory 211. The vented cover 231 further comprises a cover nozzle opening 33 through the vent end 35 of the vented cover 231.

The container 21 comprises a nozzle 25 with a trigger 26, where the nozzle 25 closes the container 21 at the nozzle end 22. The container 21 further comprises a trigger cap 27. The trigger cap 27 in use fully covers the trigger 26 to prevent accidental discharge.

The vented cover 231 connects to the container 21 and defines an accessory storage volume 41 between the vented cover 231 and the container 21. In use, the vented cover 331 receives the container 21 through the vented cover open end 34 and connects to the container 21 proximal the reservoir end 23. The vented cover 31 encloses the container 21 and not the nozzle 25 within the accessory storage volume 41.

When the vented cover 31 is in use, the nozzle 25 and the trigger cap 27 protrude through the accessory nozzle opening 12 and through the cover nozzle opening 33 so that the nozzle 25 and the trigger cap 27 are accessible when the vented cover 231 is in use.

Figure 8:
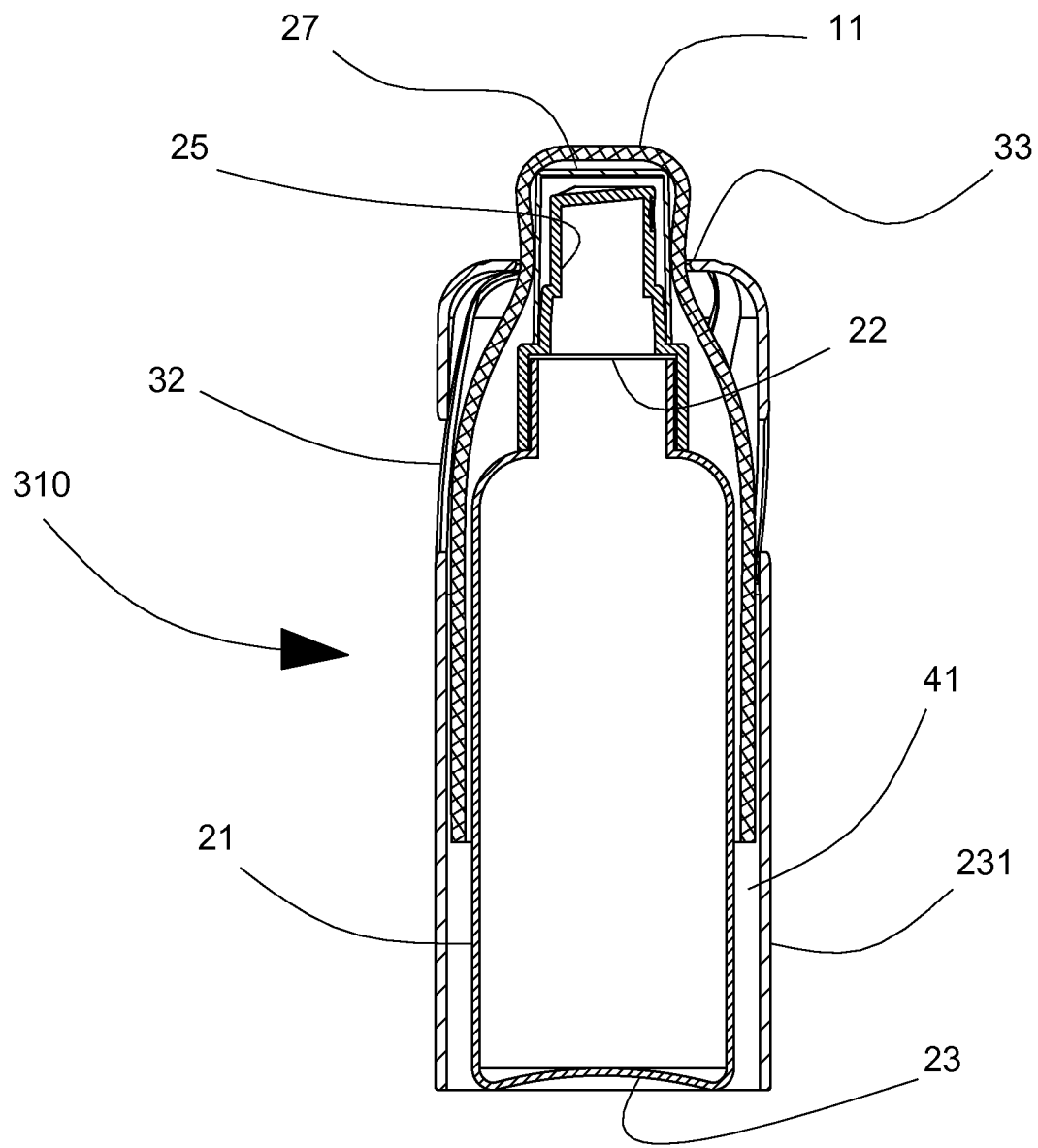
FIG. 8 is a side section view of another embodiment.

In the embodiment shown in FIG. 8, the dispensing device 310 comprises a vent cover 231 having a cover nozzle opening 33 and a dispensing accessory 11 with no accessory nozzle opening. When the vented cover 231 is in use, the nozzle 25 and the trigger cap 27 protrude through the cover nozzle opening 33 but are covered by the dispensing accessory 11. The dispensing accessory 11 drapes over the nozzle 25 and the trigger cap 27 and passes into the accessory storage volume 41 through the cover nozzle opening 33 to be confined within the storage volume 41.

The dispenser of the present invention finds many uses. A very important use is to clean the screens of computer devices such as monitors, laptop screens, smart-phone screens and any other type of computer screen.

Other uses can be for household cleaners, glass cleaner, furniture polish, multi-surface cleaner, glasses cleaner, motorcycle glasses cleaner, windshield cleaner, portable cleaners for cars, leather cleaner. In addition, the present invention finds application in shoe polish dispensers, face-wash—travel version, makeup remover—travel version, jewelry cleaner, body wash, shaving cream and the like. Any portable cleaner or liquid dispenser with a cloth that needs to be stored or dried is within the scope of the present invention.

Figure 9:
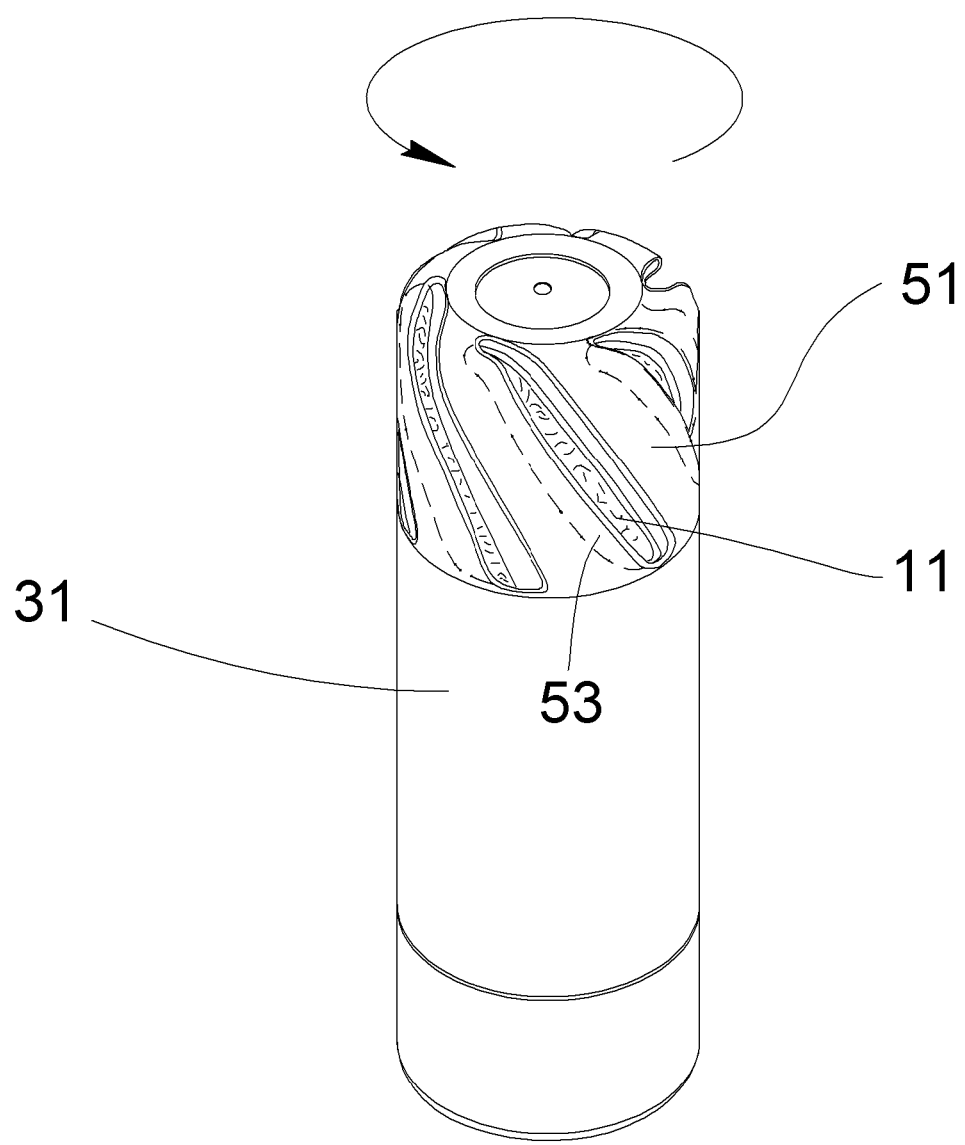
FIG. 9 shows an embodiment with a rotating outer cap.

FIG. 9 shows an alternative embodiment of the invention. The cap includes an inner cap 53 with vent openings or slots similar to what has been previously described with a rotating outer cap 51 that covers the inner cap 53 and can block or cover the inner slots in some positions of rotations and either partially, or totally, expose them in other positions of rotation. This allows the cloth 11 to dry in the open position, but protects it from dirt and grime in the closed position. The second cap 51 can fit over the inner cap 53 and rotate about the axis of the bottle 31. In the open position, the slots are typically wide open and air can easily pass through the cap and dry the cloth 11. When the outer cap 51 is in the closed position, the solid material between the slots on the outer cap can completely cover the slots to block dirt, grime, oil and other contaminates. The outer cap 51 can optionally have a detent where it can be clicked into the closed position to hold it and to assure the user that the cap is closed.

Figure 10:
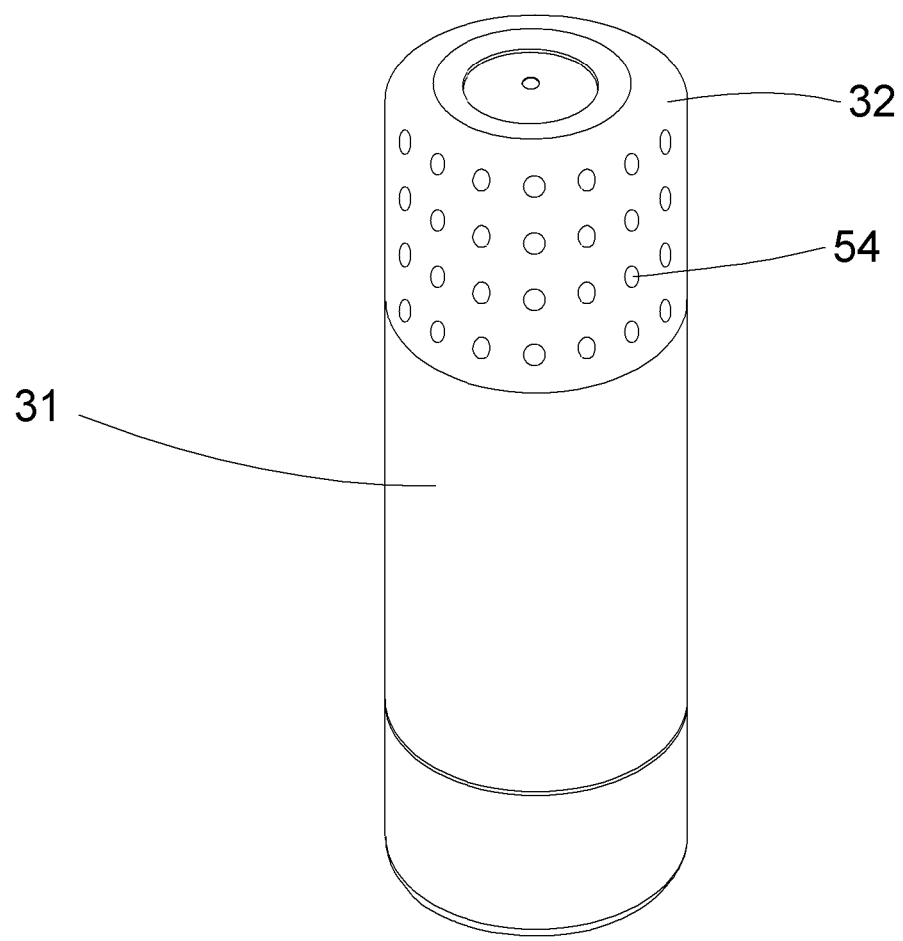
FIG. 10 shows an embodiment with a plurality of holes.

FIG. 10 shows an embodiment of the invention with a perforated cap 32. The cap can contain a number of holes or perforations 54 rather than the slots of previous embodiments. This embodiment is less expensive and easier to manufacture since it only requires one fixed cap 54 on the bottle 31 and likely no side action on the mold if made via injection molding.

Figure 11:
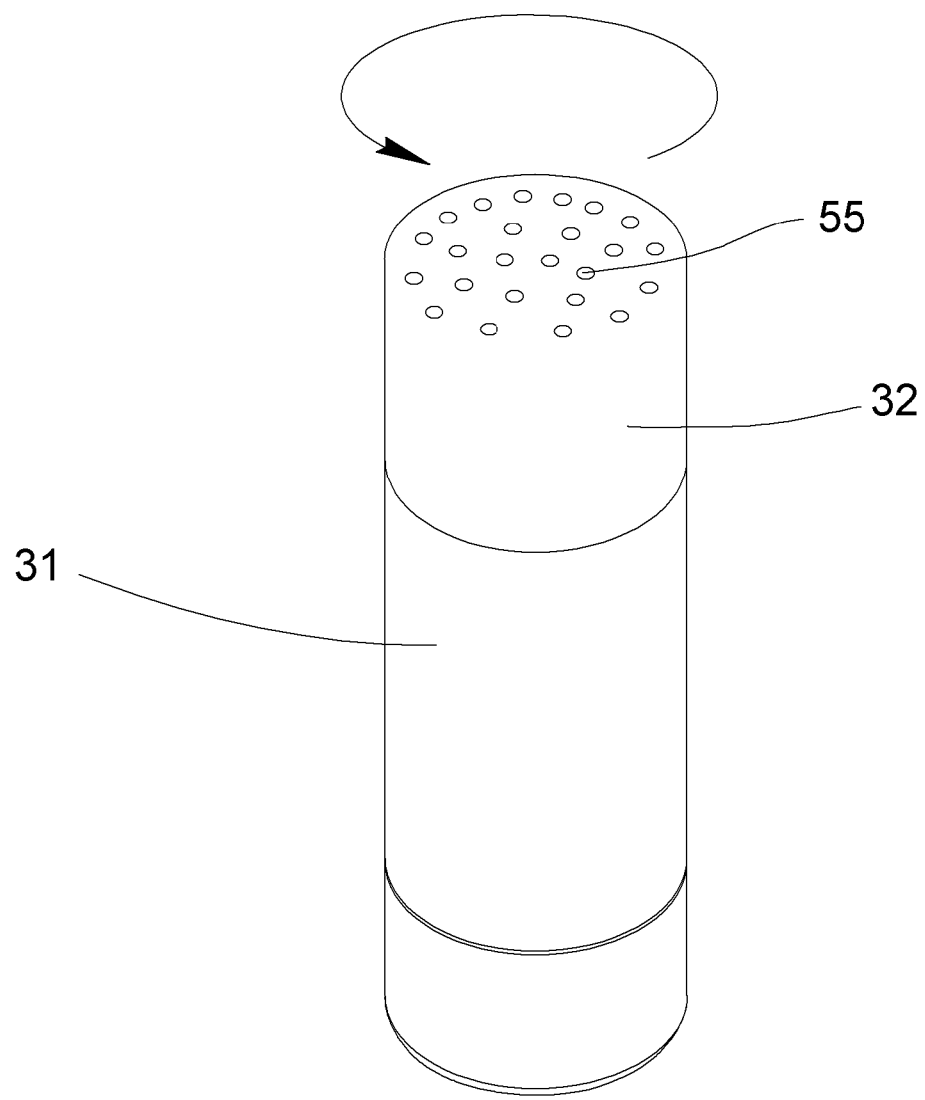
FIG. 11 shows an embodiment with holes on the top and a rotating outer cap.

FIG. 11 shows an embodiment with a perforations 55 in the top of the cap, but with an inner cap also containing similar perforations. When the outer cap is rotated, the outer perforations 55 can miss-align with the inner ones closing the cap, and hence protecting from dirt and grime.

Figure 12:
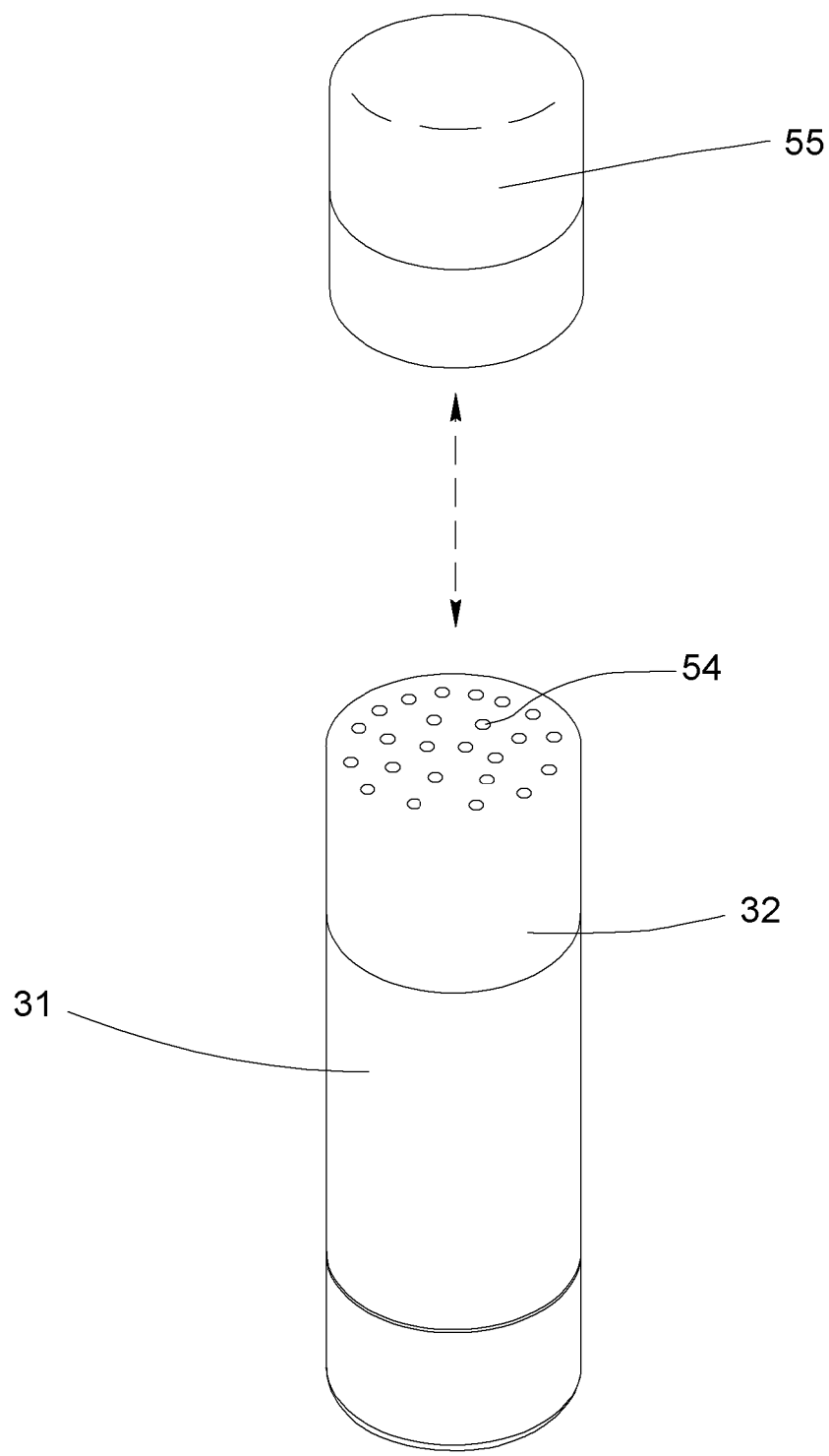
FIG. 12 shows an embodiment with holes and a removable solid outer cap.

An alternative to the embodiment of FIG. 11 is shown in FIG. 12. Here, a single cap 32 with perforations 54 is fixed, and a removable second cap 55 slides down over the fixed cap 32 closing the holes 54. This has the advantage of being cheaper and easier to manufacture than a rotating cap.

Figure 13:
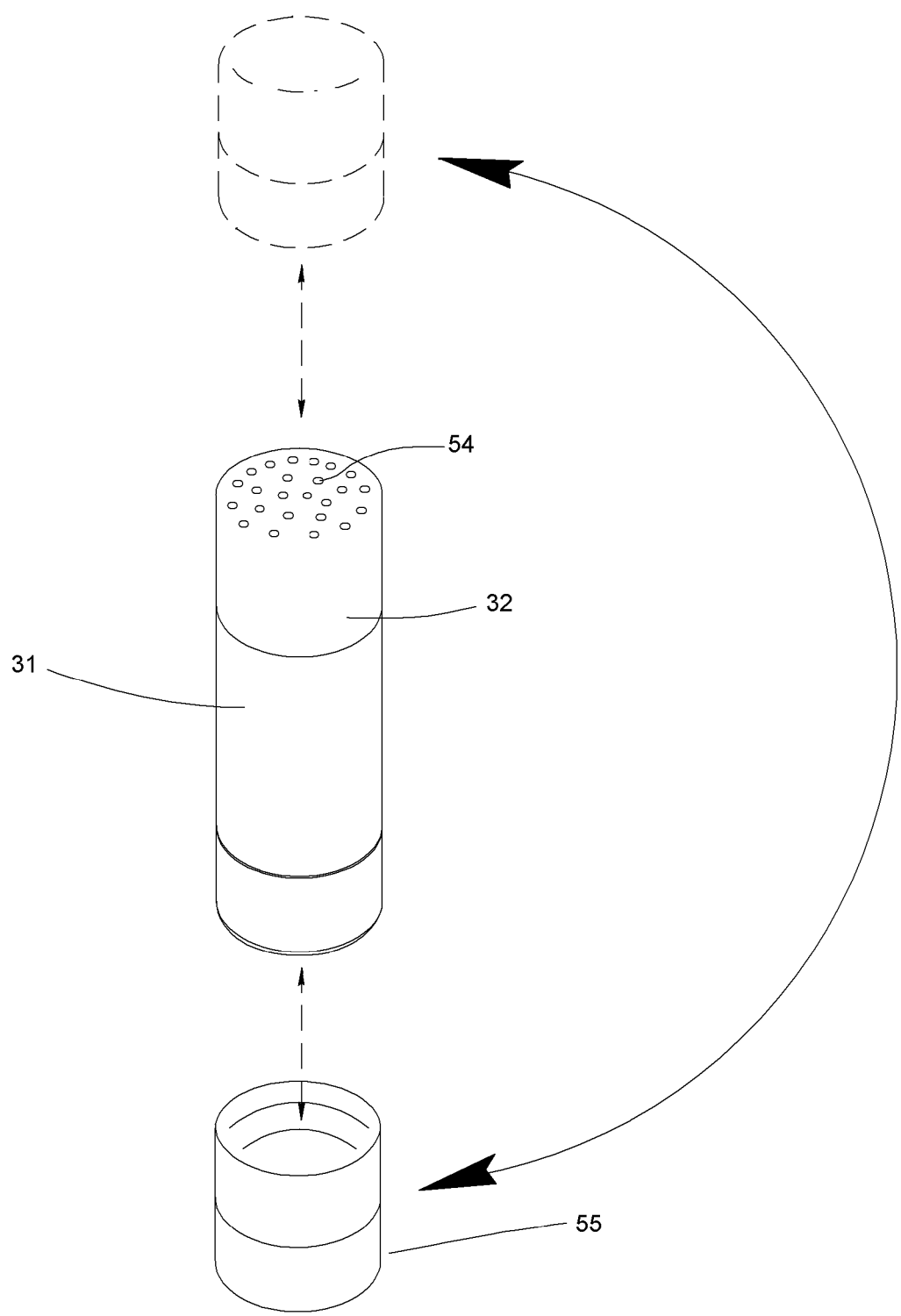
FIG. 13 shows storing the outer cap of FIG. 12 on the bottom of the container.

FIG. 13 show the embodiment of FIG. 12 where the cap 55 can be stored on the bottom of the bottle 31 when not in use simply by slipping it over the bottom end.

Figure 14:
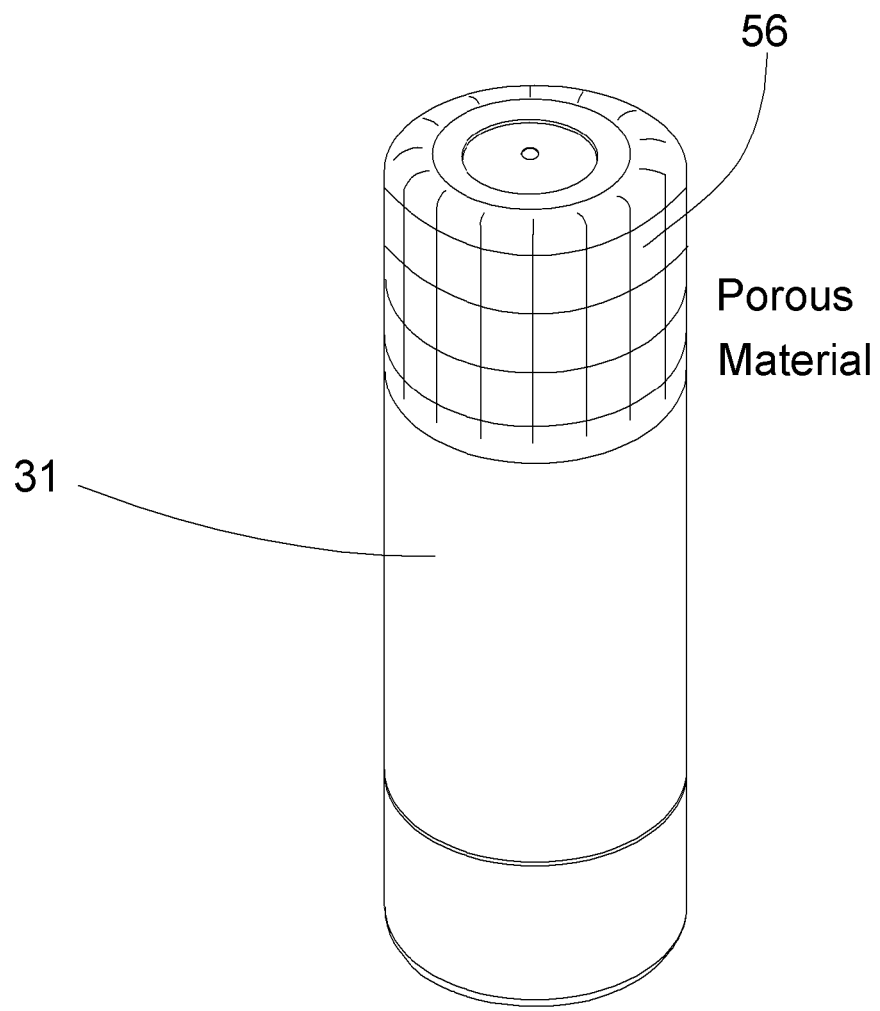
FIG. 14 shows a porous cap.

FIG. 14 shows an alternative embodiment with a single fixed cap 56 that is made of a porous material. The pore size can be large enough to allow air in and moisture out, but small enough to prevent or reduce entry of dirt, most dust, oil and the like.

Several descriptions and illustrations have been presented to aid in understanding the present invention. One with skill in the art will realize that numerous changes and variations can be made without departing from the spirit of the invention. Each of these changes and variations is within the scope of the present invention.

We claim:

1. A vented dispensing device comprising:

a dispenser with a top end and a bottom end having a dispensing nozzle constructed to dispense liquid contents;

a removable vented cover constructed to fit on the top end of the dispenser over the dispensing nozzle and having a plurality of vent openings constructed to retain a wipe cloth draped over the dispensing nozzle in a storage configuration;

the vented cover, when fitted over the top end of the dispenser, defining a storage volume between the vented cover and the dispenser, the vented cover removable to allow independent removal of the wipe cloth in a use configuration and to store and dry the wipe cloth in the storage configuration;

wherein, the wipe cloth is not attached to the dispenser or the dispensing nozzle; and wherein, the vented cover and the wipe cloth must both be removed to dispense liquid from the nozzle.

2. The dispensing device of claim 1 wherein the wipe cloth is a towel.

3. The dispensing device of claim 1 wherein the vent openings are substantially uniformly distributed around the vented cover.

4. The dispensing device of claim 1 wherein said dispenser is connected to a dispensing pump.

5. The dispensing device of claim 1 wherein the contents are under pressure.

6. The dispensing apparatus of claim 1 wherein the removable vented cover is constructed to fit on the bottom end of the dispenser when removed from the top end of the dispenser.

7. A vented dispensing device comprising:

a dispenser with a top end and a bottom end having a dispensing nozzle constructed to dispense liquid contents;

a removable vented cover constructed to fit on the top end of the dispenser over the dispensing nozzle and having a plurality of vent openings constructed to retain a wipe cloth draped over the dispensing nozzle in a storage configuration;

the vented cover, when fitted over the top end of the dispenser, defining a storage volume between the vented cover and the dispenser, the vented cover removable to allow independent removal of the wipe cloth in a use configuration and to store and dry the wipe cloth in the storage configuration;

wherein, the wipe cloth is not attached to the dispenser or dispensing nozzle, and liquid cannot be dispensed through the wipe cloth; and wherein, the vented cover and the wipe cloth must both be removed to dispense liquid from the nozzle.

8. The dispensing apparatus of claim 7 wherein the removable vented cover is constructed to fit on the bottom end of the dispenser when removed from the top end of the dispenser.

\* \* \* \* \*